United States Patent [19]

Drake et al.

[11] Patent Number: 4,849,001
[45] Date of Patent: Jul. 18, 1989

[54] METHOD FOR MAKING SINTERED GLASS

[75] Inventors: Cyril F. Drake, Harlow; Alfred J. Arch, Ongar; Mary Tripp, Bishop's Stortford, all of Great Britain

[73] Assignee: STC PLC, London, United Kingdom

[21] Appl. No.: 94,879

[22] PCT Filed: Oct. 22, 1986

[86] PCT No.: PCT/GB86/00648

§ 371 Date: Aug. 19, 1987

§ 102(e) Date: Aug. 19, 1987

[87] PCT Pub. No.: WO87/02657

PCT Pub. Date: May 7, 1987

[30] Foreign Application Priority Data

Oct. 23, 1985 [GB] United Kingdom ................. 8526124

[51] Int. Cl.$^4$ ........................ C03C 11/00; C03B 19/06
[52] U.S. Cl. .................................... 65/18.3; 65/18.4; 65/22; 65/134; 501/45
[58] Field of Search ........................ 65/18.3, 18.4, 102, 65/104, 134, 22; 501/45

[56] References Cited

U.S. PATENT DOCUMENTS

| 1,654,404 | 12/1927 | Blumenberg | 501/45 |
| 2,390,354 | 12/1945 | Clapp | 65/18.3 X |
| 4,165,226 | 8/1979 | Kita | 65/18.3 X |
| 4,645,749 | 2/1987 | Drake | 501/45 |

FOREIGN PATENT DOCUMENTS

| 0140538 | 5/1985 | European Pat. Off. . |
| 0147932 | 7/1985 | European Pat. Off. . |
| 2020327 | 11/1971 | Fed. Rep. of Germany . |
| 85/01210 | 3/1985 | PCT Int'l Appl. . |

Primary Examiner—Robert L. Lindsay
Attorney, Agent, or Firm—Lee & Smith

[57] ABSTRACT

A porous water soluble glass body is formed by sintering powdered glass, compacted to a predetermined density, at a temperature near the glass softening temperature ($T_s$). The porous body may be impregnated with an organic material for subsequent release at a rate determined by the glass solubility.

11 Claims, 2 Drawing Sheets

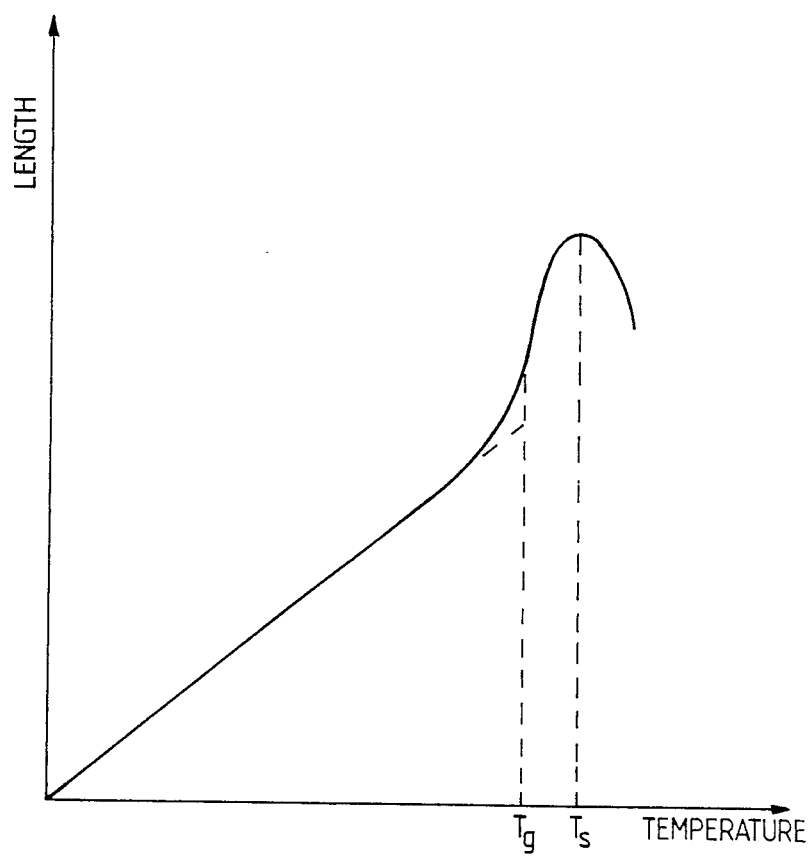

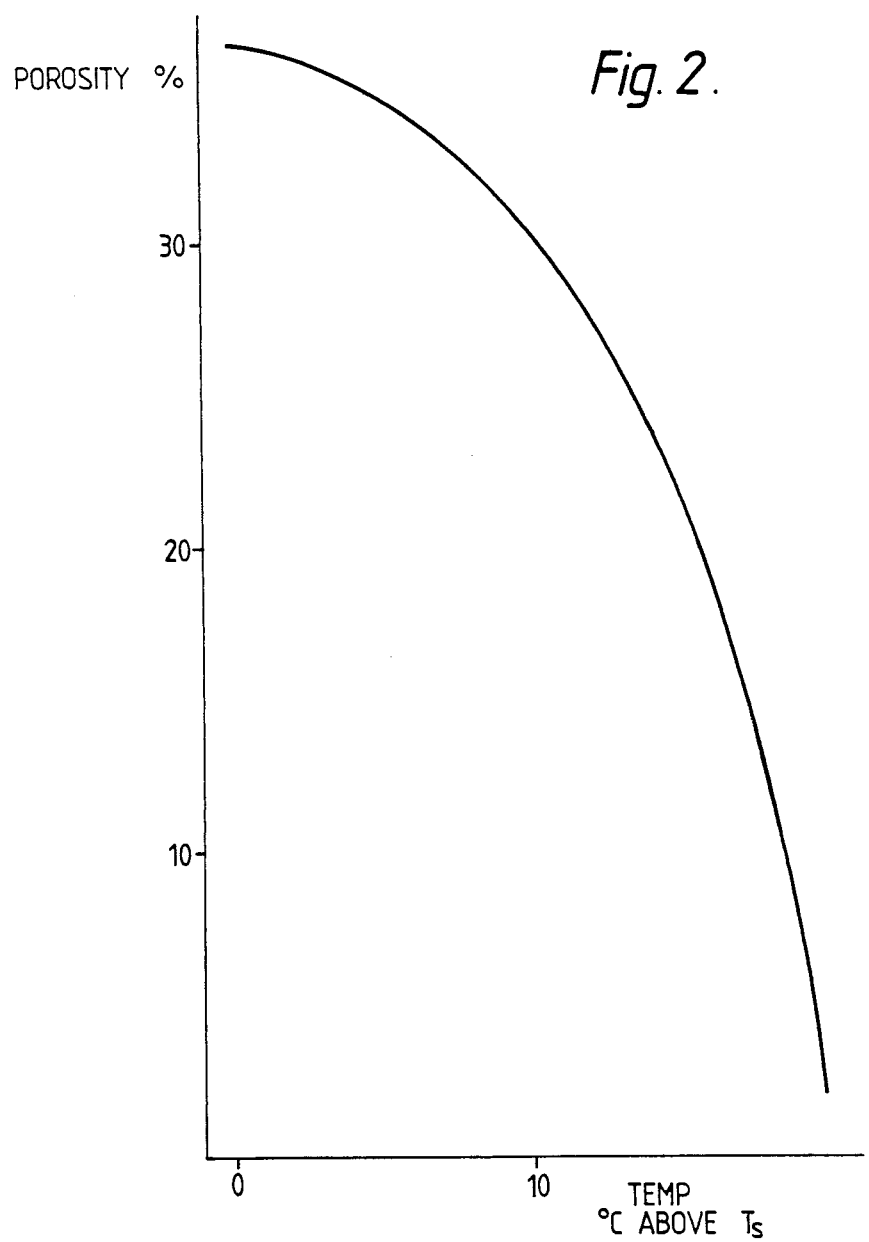

METHOD FOR MAKING SINTERED GLASS

This invention relates to methods of forming sintered glass bodies and to glass bodies formed by such methods.

Water soluble glass compositions have been used to provide controlled dissolution of active materials incorporated in the compositions. When the active material is inorganic it can generally be incorporated, e.g. in oxide form, in the glass composition. Organic materials however degrade at glass melting temperatures and cannot therefore be incorporated in the glass itself. In an attempt to overcome this problem it has been proposed to provide a sintered glass body the pores of which are filled with an organic material.

Conventional sintering processes, such as are used in powder metallurgy, operate at high temperatures, e.g. 1000° C., and typically require a free volume in the sintered products of less than 2%. These processes cannot be used to sinter glass compositions which flow at relatively low temperatures, typically 300° to 400° C. In addition, these prior art techniques are not suitable for the production of small and/or intricately shaped devices owing to the fagility of the powder perform prior to sintering. Handling problems preclude the application of mass production techniques. Furthermore, in order to provide sufficient porosity for receiving a filling material, a large free volume is required. Conventional processes provide a high degree of compaction prior to the sintering stage.

The object of the present invention is to minimise or to overcome these disadvantages.

According to the invention there is provided a method of forming a sintered water soluble glass body, the method including providing a water soluble glass in particulate form, compacting the glass particles together with a binder to form a self-supporting porous body, and heating the body to a temperature above Ts-10° C. where Ts is the dilatometric softening temperature of the glass, the temperature not exceeding the denitrification temperature of the glass.

According to a further aspect of the invention there is provided a device for the controlled release of an active constituent and comprising a sintered glass body as defined in the above preceding paragraph and having pores containing the active constituent.

Embodiments of the invention will now be described with reference to the accompanying drawings in which:

FIG. 1 ilustrates the thermal expansion properties of a glass, and FIG. 2 illustrates the relationship between sintering temperature and porosity.

The porosity of the body prior to sintering is determined by the compaction pressure and by the particle size distribution of the glass. Thus, a very wide size distribution results in a low porosity. Advantageously the glass particles are sieved to provide a fraction within a predetermined particle size range. For example, we have found that, by providing a glass powder of substantially uniform particle size a free volume as high as 45% can be obtained prior to sintering. It will be appreciated that, by providing predetermined proportions of various sieve fractions the free volume prior to sintering can be controlled to a desired value. For example, by increasing the proportion of finer sieve fractions, the free volume or porosity may be reduced and vice versa.

Typically a powder water soluble glass is sieved to provide a material of substantially uniform particle size. The powder is then treated with a binder. For this purpose we prefer to employ a material that is either volatile or decomposes to volatile material at a temperature no greater than the subsequent firing temperature of the sinter. We have successfully employed camphor, which is volatile, and nitrocellulose, which decomposes to carbon dioxide, water and nitrogen, for this purpose but other materials, for example naphthalene, can of course be used. The binder may be applied to the powder in a solvent, the solvent being allowed to evaporate prior to further processing.

The treated powder is next placed in a mould and compacted under pressure to form a porous body. High pressure is not required as it is necessary only to compact the powder sufficiently to form a self-supporting body. Typically we employ pressures between 10 and 100 lb/inch$^2$. The compaction pressure determines the porosity or free volume of the 'green' compact prior to sintering. The maximum free volume that can be achieved is 45% as this is the limit beyond which the compact becomes too fragile to permit further processing.

The green compact is sintered at a temperature between Ts-10° C. and Ts+100° C., and preferably between Tg-10 and Ts+25° C. where Ts is the dilatometric softening temperature of the glass. Advantageously the sinter temperature is equal to or above Ts. The thermal characteristics of a typical glass composition are shown in FIG. 1 of the accompanying drawings, which shows a graph of the thermal expansion of a glass. A glass specimen is heated slowly, typically at 3° C.-min$^{-1}$, in a quartz dilatometer. One face of the specimen is supported on a silica platform and the movement of the end of a silica push-rod held in contact with the opposite face by a light pressure is detected by a sensitive optical or electromagnetic sensor. Thus the length of the specimen is continuously monitored. As the temperature is raised from room temperature the specimen at first expands at a constant rate. At an elevated temperature the expansion coefficient of the glass increases. Eventually the glass 'softens' and the load on the push rod is sufficient for it to start penetrating the glass. The temperature corresponding to the intersection of the extrapolated lines of region I and II is known as the glass transition or glass transformation temperature and is shown on the figure as $T_g$. The softening point $T_s$ is defined as the temperature at which the push rod starts to penetrate the glass.

During sintering the compact generally shrinks in volume and the porosity or free volume thus decreases. The magnitude of this shrinkage is determined by the sintering temperature and time. Thus, higher sintering temperatures and longer sintering times cause a reduction in porosity. The binder is driven off during this sintering process. In some cases we have observed a small increase in free volume. This is thought to be due to outgassing from the binder residues in the compact. In some applications the compact may be subjected to a prebake, e.g. by heating to a temperature of 100° to 150° C. for 1 to 2 hours, to remove both solvent residue and surplus binder. We have found that the compact is still self supporting after this treatment.

As previously stated the ultimate free volume is determined by the sintering temperature, this effect being illustrated in FIG. 2 of the accompanying drawings. It will be appreciated that the precise sintering characteristics will depend on the nature of the glass and that, in individual cases, will be determined by experiment.

After sintering is completed it is preferred that the sintered body is annealed by cooling at a controlled rate to ambient temperature. Typically cooling is effected at a rate of 10° to 100° C. per hour, and preferably 20° to 30° C. per hour. In general, larger sintered bodies require slower cooling rates.

During sintering, some glasses whose compositions are close to the glass forming region limits may display a tendency to devitrify. For this reason we prefer to employ sintering temeperatures that are at least 100° C. below the denitrification temperature of the glass. Alternatively, or in addition, any tendency to denitrification may be overcome by the incorporation of one or more further glass modifying oxides in the glass. Thus, for example, a water soluble sodium/calcium/phosphate glass may be protected against devitrification by the replacement of up to 5 mole % of the calcium oxide with magnesium oxide, zinc oxide or mixtures thereof. Alternatively, the proportion of $P_2O_5$ may be increased to move the composition further away from the glass-forming boundary on the phase diagram. The resultant change in dissolution rate may be compensated by an appropriate alteration of the sodium oxide content of the glass.

The porous sintered glass body may be filled with an organic material in liquid form or in solution by capillary action. Under ambient pressure conditions over 90% of the free volume of the porous body can be filled in this way whilst under vacuum a substantially complete fill may be achieved.

The following examples illustrate the invention.

EXAMPLE 1

A water soluble glass was prepared having the following molar composition

| $Na_2O$ | 44% |
| --- | --- |
| $CaO$ | 6% |
| $MgO$ | 5% |
| $P_2O_5$ | 45% |

The dissolution rate in distilled water at 38° C. was 7.0 mg/cm²/h. Dilatometric measurement of the thermal characteristics of the glass showed Tg to be 304° C. and Ts to be 318° C.

The glass was sieved to provide a powder classified as +45 microns −170 microns and 100 g of this powder was treated with a solution of 5 g camphor ($C_{10}H_{16}O$) in 100 ml propan-2-ol. Sample quantities weighing 4.75 g of the treated powder were pressed into discs of 2.5 cm diameter and 0.55 cm in thickness corresponding to a compaction of about 68% of the density of the glass. The compacts were heated in air at 150° C. for 30 minutes to drive off the solvent and were then sintered at temperatures between 320° C. and 337° C. for a further 30 minutes. The sintered discs were then annealed by cooling at a rate of 25° C./hr. The porosity (free volume) of each disc was measured by determining its soak-up of white spirit. The results are summarised in Table 1 below.

TABLE 1

| Sinter Temperature | Porosity % |
| --- | --- |
| 337 | 7 |
| 334 | 25 |
| 330 | 27 |

TABLE 1-continued

| Sinter Temperature | Porosity % |
| --- | --- |
| 329 | 26 |
| 324 | 34 |
| 320 | 36 |

EXAMPLE 2

A glass was prepared by fusion of a mixture comparing the following batch weights:

| $NaH_2PO_4$ | 809 g |
| --- | --- |
| $CaHPO_4$ | 132 g |
| $CO_3$ | 153 g |
| $Na_2$ | |

Analysis of the glass provided the following molar composition:

| $Na_2O$ | 50.3% |
| --- | --- |
| $Ca_O$ | 10.2% |
| $P_2O_5$ | 39.5% |

Dilatometric measurement of the thermal characteristics of the glass showed $T_s$ to be 310° C. The dissolution rate in distilled water at 38° C. was 120mg/cm²/h.

A quantity of the glass was crushed and sieved to remove all particles larger than 180 microns. The sieved powder was then mixed with 2 weight percent camphor and pressed into discs as before with a pressure of 100 pounds per square inch. The discs were baked at a temperature of 150° C. for 2 hours and were sintered at a temperature of 348° C. for 1 hour. They were then cooled to ambient temperature at a rate of 25° C. per hour. The average porosity of the discs measured by determining soak-up of white spirit was 6 volume percent.

EXAMPLE 3

Two glass compositions were prepared during the following minor compositions:

| Glass A | $Na_2O$ | 40 | Solution rate |
| --- | --- | --- | --- |
|  | $Ca_O$ | 12 | 2.8 mg/cm²/h at 38° C. |
|  | $P_2O_5$ | 45 | in distilled water |
|  | $MgO$ | 3 | |
| Glass B | $Na_2O$ | 40.3 | Solution rate |
|  | $Ca_O$ | 12.1 | 2.0 mg/cm²/h at 38° C. |
|  | $P_2O_5$ | 44.5 | in distilled water. |
|  | $MgO$ | 3.1 | |

The glass was ground and graded to obtain selected particle size ranges, and the sieve fractions mixed in given proportions to provide a material suitable for the preparation of discs. The proportions of the sieve fractions are listed in Table II below.

TABLE II

Particle Size Distribution of Glass Powder

| | Wt % Used | |
| --- | --- | --- |
| Sieve Fraction um | Glass A | Glass B |
| 170–150 | 40 | 50 |
| 150–125 | 10 | 10 |
| 125–106 | 10 | 10 |
| 106–75 | 25 | 20 |
| 75–45 | 10 | 5 |

TABLE II-continued

| Particle Size Distribution of Glass Powder | | |
|---|---|---|
| | Wt % Used | |
| Sieve Fraction um | Glass A | Glass B |
| Less tnan 45 | 5 | 5 |

The glass powders were then pressed into discs by the following process.

To 500 gm of the glass powder mix, a solution of 5 gms camphor dissolved in 50 ml diethyl ether was added and the mixture thoroughly stirred. The ether was evaporated to provide a free flowing powder. Discs were prepared from the glass powder/camphor mixture by pressing a weighed quantity in a split metal die to a given thickness using a fly press. The weight of mixture per disc was 4.75 gms.

Pressed discs were heated at 150° C. for 1 hour followed by a sintering cycle of 330° C. for 1 hour and cooled to room temperature at a ramp rate of 25° C./hour. All operations were carried out in air. The average porosity of the sintered discs measured by the white spirit method was found to be 32% for each glass.

These results illustrate the feasibility of forming sintered water soluble glass bodies using the technique described herein.

The porous bodies formed by the process described herein are of particular application in the construction of rumen boluses, but they may of course be used in other applications for the controlled release of active materials.

I claim:

1. A method of forming a sintered water soluble glass body, the method including providing a water soluble glass in particulate form, applying a binder to the glass particles, subjecting the glass particles together with the binder to a pressure of 10 to 100 pounds per square inch whereby to form a self supporting porous structure, and heating the porous structure to a temperature above $T_s - 10°$ C. where $T_s$ is the dilatometric softening temperature of the glass whereby to form the porous glass body, the temperature not exceeding the devitrification temperature of the glass.

2. A method as claimed in claim 1, wherein said binder is volatile or decomposes to volatile materials at a temperature at or below the sintering temperature.

3. A method as claimed in claim 2 wherein the binder is camphor.

4. A method as claimed in claim 2 wherein the binder is nitrocellulose or naphthalene.

5. A method as claimed in claim 1, wherein the sintered body is cooled at a substantially constant rate to ambient temperature.

6. A method as claimed in claim 5, wherein the body is cooled at a rate of 10° to 100° C. per hour.

7. A method as claimed in claim 1 wherein the body is sintered at a temperature at least 100° C. below the glass devitrification temperature.

8. A method as claimed in claim 1, wherein the body is sintered at a temperature in the range $Tg - 10°$ C. to $Tg + 25°$ C.

9. A method as claimed in claim 8, wherein the body is sintered at a temperature at or above the softening temperature (Ts).

10. A method as claimed in claim 1, wherein the sintered water soluble glass body comprises a rumen bolus.

11. A method as claimed in claim 1, wherein the glass comprises a phosphate glass.

* * * * *